United States Patent [19]

Olsson et al.

[11] Patent Number: 5,043,325
[45] Date of Patent: Aug. 27, 1991

[54] N-6 SUBSTITUTED ADENOSINE DERIVATIVES AS CARDIAC VASODILATORS

[75] Inventors: Ray A. Olsson, Odessa; Robert D. Thompson, Tampa, both of Fla.

[73] Assignee: Whitby Research, Inc., Irvine, Calif.

[21] Appl. No.: 829,285

[22] Filed: Feb. 13, 1986

Related U.S. Application Data

[63] Continuation of Ser. No. 601,435, Apr. 18, 1984, abandoned.

[51] Int. Cl.$^5$ ............................................. A61K 31/70
[52] U.S. Cl. ....................................... 514/46; 514/45; 536/26; 536/24
[58] Field of Search ............................ 514/46; 536/26

[56] References Cited

U.S. PATENT DOCUMENTS

| | | | |
|---|---|---|---|
| 2,881,164 | 4/1959 | Kissman et al. | 536/26 |
| 3,502,649 | 3/1970 | Thiel et al. | 536/26 |
| 3,509,129 | 4/1970 | Kampe et al. | 536/26 |
| 3,590,029 | 6/1971 | Koch et al. | 536/26 |
| 3,851,056 | 11/1974 | Stork et al. | 514/46 |
| 3,901,876 | 8/1975 | Vorbrügger et al. | 536/26 |
| 3,966,916 | 6/1976 | Kampe et al. | 514/46 |
| 4,029,884 | 6/1977 | Stein et al. | 536/26 |
| 4,081,534 | 3/1978 | Elion et al. | |
| 4,090,021 | 5/1978 | Vorbruggen | |
| 4,167,565 | 9/1979 | Stein et al. | |
| 4,189,485 | 2/1980 | Matsuno et al. | |
| 4,224,438 | 9/1980 | Fauland et al. | |
| 4,495,180 | 1/1985 | Alexander | |
| 4,514,405 | 4/1985 | Irmscher et al. | 514/46 |

FOREIGN PATENT DOCUMENTS

| | | | |
|---|---|---|---|
| 2007273 | 8/1971 | Fed. Rep. of Germany | 514/46 |
| 2139107 | 2/1973 | Fed. Rep. of Germany | 536/26 |
| 2426682 | 12/1975 | Fed. Rep. of Germany | 536/26 |

OTHER PUBLICATIONS

Prasad, et al, "Modification of the 5'Position of Purine Nucleosides, 2, Synthesis and Some Cardiovascular Properties of Adenosine-5'-(N-substituted)carboxazmides", *J. Med. Chem.* 1980, 23, 313–319.
Stein et al, "Cardiovascular Effects of Nucleoside Analogs", *Annals New York Acad. Sciences* (1975) 225, 380–389.
Stein, "Ethyl Adenosine-5'carboxylate, A Potent Vasoactive Agent in the Dog", *J. Med. Chem.* (1973) 16:11, 1306–1208.
Schwabe, "General Aspects of Binding of Ligands to Adenosine Receptors", Chap. 6 *Regulatory Function of Adenoisie,* Berne et al, 77–96 (1983).
Ukena, et al, 6–substituted 9–methyladenines: A New Class of Adenosine Receptor Antagonists", *FEBS Lett.,* 215 (2) 203–208 (1987).
Robins et al, "Potential Purine Antagonists IV. Synthesis of Some 9-Methyl-6-substituted-purines", *J. Am. Chem. Soc.,* 79, 490–494 (1957).
Montgomery, et al, "Synthesis of Potential Anticancer Agents, IX,9-Ethyl-6-substituted-purines", *J. Am. Chem. Soc.,* 79, 5238–5242 (1957).
Myers, et al, "Alkylation of the Purine Nucleus by Means of Quaternary Ammonium Compounds, I. Tetraalkylammonium Hydroxides", *J. Org. Chem.,* 28, 2089–2089 (1963).
Fox, et al, "Binding Characteristics of an Adenosine, Receptor in Human Placenta", *J. Biol. Chem.,* 258(11), 6952–6955 (1983).

*Primary Examiner*—Johnnie R. Brown
*Assistant Examiner*—L. Eric Crane
*Attorney, Agent, or Firm*—Walter A. Hackler; Robert J. Baran

[57] ABSTRACT

New, N-6 monosubstituted adenosine derivatives are disclosed which have significant cardiac vasodilatory effect. The compounds of the invention include 6-(cyclo-butyl amino)-9-($\beta$-D-ribofuranosyl)-9H-purine, 6-(2-methyl-2-phenyl hydrazino)-9-($\beta$-D-ribofuranosyl)-9H-purine, and compounds of the general formula:

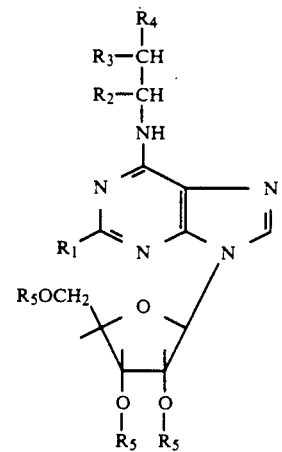

wherein $R_1$ is H, lower alkyl, lower alkoxy, alkylamino, or arylamino, $R_2$ is H, lower alkyl, hydroxymethyl, phenyl or substituted phenyl, $R_3$ is H. lower alkyl, phenyl, substituted phenyl, $R_3$ is H, lower alkyl, phenyl, substituted phenyl, 2 or 3-thienyl, or 2 or 3-pyridyl, $R_4$ is H or lower alkyl, and $R_5$ is H or lower acyl. Particularly active as a cardiac vasodilator is the compound (-)-6-(R-1-phenyl-2-butyl amino)-9-($\beta$-D-ribofuranosyl)-9H-purine.

26 Claims, No Drawings

N-6 SUBSTITUTED ADENOSINE DERIVATIVES AS CARDIAC VASODILATORS

CROSS-REFERENCE TO RELATED APPLICATIONS

This is a continuation of application Ser. No. 601,435 filed Apr. 18, 1984, now abandoned.

BACKGROUND OF THE INVENTION

1. Field of the Invention

The present invention is directed to certain N-6 substituted adenosine derivatives which have beneficial cardiovascular activity in mammals, including humans and domestic animals 2. Brief Description of the Prior Art Cardiovascular activities of adenosine, and of certain of its derivatives, have been known in the art. German Offenlegungschrift Nos. 2133273, 2426682, 1795761, 1913818, 2007273, 2238923, 2060189, 2244328, 1814711, 2136624, South African Patent Application No. 677630 (filed Dec. 20, 1967) and British Patent Specification No. 1,123,245 describe adenosine derivatives which have cardiovascular, coronary dilator or antilipolytic activities.

In an article titled "Coronary Vasoactivity of Adenosine in the Conscious Dog" Olsson et al. describe a bioassay of compounds for cardiovascular activity. In the assay, the compounds to be tested are infused intracoronarily into conscious, healthy dogs. The naturally occurring nucleoside adenosine has a demonstrable coronary dilator effect under these conditions. The concentration of the test compound infused into the dog's heart, which causes half-maximal coronary vasodilation is designated $ED_{50}$.

More specifically, under the conditions of this assay, $ED_{50}$ is determined in the following manner. Late diastolic coronary conductance (LDCC of the experimental dog is monitored through suitable instrumentation. Late diastolic coronary conductance is measured at maximum coronary vasodilation (peak reactive hyperemia), and is designated $LDCC_{max}$. Late diastolic coronary conductance is also measured at basal coronary vasodilation, and is designated $LDCC_o$.

The difference between instantaneously measured late diastolic coronary (LDCC) and basal late diastolic coronary conductance ($LDCC_o$) is expressed as a fraction of the difference between maximum late diastolic coronary conductance ($LDCC_{max}$) and basal late diastolic coronary conductance ($LDCC_o$). Thus $\Delta LDCC$ is defined by Equation I.

$$\Delta LDCC = \frac{LDCC - LDCC_0}{LDCC_{max} - LDCC_o} \quad \text{EQUATION I}$$

As the concentration of the tested compound is varied, and the corresponding $\Delta LDCC$ is obtained through measurements and the above-summarized calculations, data of an "$\Delta LDCC$ versus concentration" function or plot are obtained.

$ED_{50}$ is derived from these data by log-logit transformation of the "$\Delta LDCC$ versus concentration" plot; namely by solving the linear regression of logit ($\Delta LDCC$) on log (concentration) for $\Delta LDCC=0.5$.

$ED_{50}$ of tested compounds was found to provide good comparison with data of the same or another compound tested on a different experimental dog, when the $ED_{50}$ of the particular compound is related to $ED_{50}$ of adenosine in the same experimental dog. As is set forth in Equation II, molar potency ration (MPR) is defined as the ratio of $ED_{50}$ of adenosine to $ED_{50}$ of the test compound. Molar potency ration (MPR) is a useful measure of cardiovascular vasodilatory effect, and hence of the utility of the tested compound.

$$MPR = \frac{ED_{50} \text{ (adenosine)}}{ED_{50} \text{ (tested compound)}} \quad \text{EQUATION II}$$

It follows from the foregoing, that the greater is the vasodilatory effect of a tested compound, the larger is the corresponding molar potency ratio (MPR).

An article by J. W. Daly titled "Adenosine Receptors: Targets for Future Drugs", Journal of Medicinal Chemistry 25, 197 (1982) provides a summary of various theories regarding the physiological role of adenosine and of certain adenosine analogs, agonists and antagonists.

As the above referenced patents and articles demonstrate, the prior art has provided and tested a relatively large number of adenosine derivatives for cardiovascular, and vasodilatory activity. Nevertheless, such derivatives having optimal biological properties have remained an elusive goal for the prior art. As is known, optimal biological properties include significant activity, absence of undesirable side effects, and sufficient duration of the desired activity.

The present invention is a significant development in the search for such optimal compounds. Compounds of the present invention have a novel structure and possess significant cardiovascular activity thereby providing an array of cardiovascular, vasodilator agents from which compounds having optimal characteristics as drugs for a particular type of application, may be selected.

SUMMARY OF THE INVENTION

The present invention relates to new, N-6 monosubstituted adenosine derivatives which have significant cardiovascular vasodilatory activity. Compounds of the invention have the General Formula I,

GENERAL FORMULA I

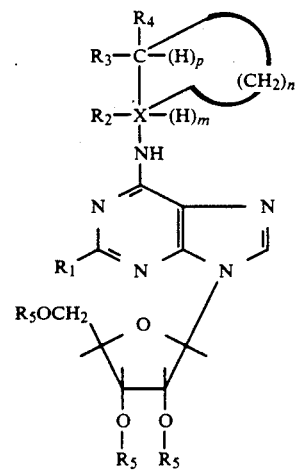

Wherein $R_1$ is H, a lower alkyl group, an alkoxy group having 1-4 carbon atoms, an alkylamino group, an arylamino group, lower alkyl substituted arylamino group, lower alkoxy substituted arylamino group, or halogen substituted arylamino group; $R_2$ is H, lower alkyl group, hydroxymethyl group, phenyl group, lower alkyl substituted phenyl group, lower alkoxy substituted phenyl group; $R_3$ is H, lower alkyl group, phenyl group, lower alkyl substituted phenyl group, monohalogen substituted phenyl group, mono-lower alkoxy substituted phenyl group, 2 or 3-thienyl group, lower alkyl substituted 2 or 3 thienyl group, lower alkoxy substituted 2 or 3-thienyl group, mono-halogen substituted 2 or 3-thienyl group, 2 or 3 pyridyl group lower alkyl substituted 2 or 3-pyridyl group, lower alkoxy substituted 2 or 3-pyridyl group, or mono-halogen substituted 2 or 3-pyridyl group; $R_4$ is H, or a lower alkyl group; $R_5$ is H, or an acyl group having 1-4 carbons; X is C or N; n is either 0 (zero) or 2; m is either 0 (zero) or 1; p is either 0 (zero) or 1; with the provisos that when X is N then n is 0, m is 0 and p is 1; when X is C and n is 0, then m is 1 and p is 1; when X is C and n is 2, the m is 0 and p is 0; and when X is C, n is 0, $R_2$ is methyl, $R_1$ and $R_4$ are H, then $R_3$ is not phenyl.

Preferred examples within the scope of the invention are compounds of the General Formula I wherein the 2 position of the purine nucleus is unsubstituted, ($R_1$ is H). Further preferred examples are the nucleosides of General Formula I wherein the hydroxl groups of the ribofuranose moiety are unsubstituted, ($R_5$ is H).

The nucleosidic compounds of the present invention are prepared by nucleophilic displacement of a suitable leaving group (Y), such as chloro, bromo, iodo, methylmercapto, from the 6 position of the purine ribofuranosides of General Formula 2. Nucleophiles for the displacement are primary amines or hydrazino compounds of the General Formula 3.

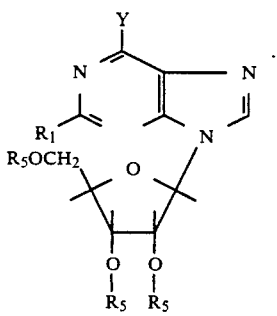

GENERAL FORMULA 2

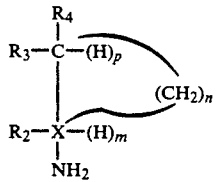

GENERAL FORMULA 3

The symbols $R_1$, $R_2$, $R_3$, $R_4$, $R_5$, X, m, n and p have the same definitions in General Formulae 2 and 3 as in General Formula 1, and Y is the leaving group. In addition, $R_5$ can be various acyl or alkali stable blocking groups commonly used in carbohydrate and nucleoside chemistry.

Nucleosidic compounds of the present invention wherein the 1-position of the purine nucleus is unsubstituted ($R_1$ is H), and wherein the first atom in the substituent of the N-6 amino group is carbon (X is C), are also prepared, in accordance with the present invention, by alkali induced rearrangement of N-1 substituted adenosines of the General Formula 4.

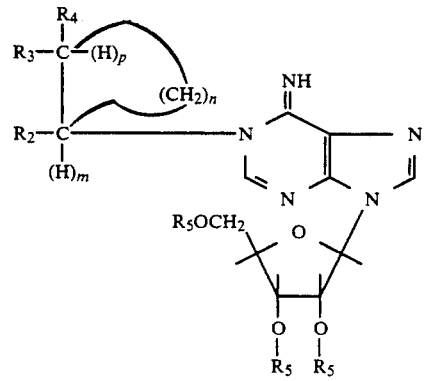

GENERAL FORMULA 4

In General Formula 4, the symbols $R_2$, $R_3$, $R_4$, m, p and n are defined as in General Formula 1. $R_5$ symbolizes the same groups as in General Formula 1, and also such alkali stable sugar hydroxyl protecting groups as benzyl, ketal or acetal groups, particularly isopropylidene or benziledene groups, which may be removed by hydrogenation or acidolysis.

The N-6 monosubstituted adenosine derivatives of the present invention are useful as cardiovascular agents and particularly as vasodilators. Specific compounds of the invention have molar potency ratios (MPR) in the range of 0.81 for 6- (4 heptylamino)-9-($\beta$-D-ribofuranosyl) -9H purine and 7.5 for (—)-6-(R-1-phenyl-2-butylamino) -9-($\beta$-D-ribofuranosyl) - 9H - purine.

DETAILED DESCRIPTION OF THE INVENTION

The compounds of the present invention have the General Formula 1. Preferred examples of compounds of the invention are N-6 monosubstituted adenosine nucleosides, namely compounds wherein the 2-position of the purine nucleus is unsubstituted; $R_1$ is H in General Formula 1. Furthermore, preferred nucleosides of the present invention have free hydroxyl groups on the ribofuranose moiety, ($R_5$ is H in General Formula 1), although nucleosides of General Formula 1 having acyl groups containing 1-4 carbon atoms are also within the scope of the present invention. As is known, such "lower" acyl groups are relatively readily split-off from nucleoside hydroxyl groups under physiological conditions.

Compounds of the present invention include, as a subgroup, nucleosides of General Formula 5.

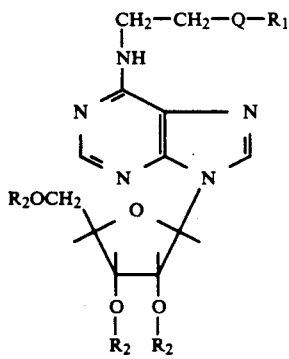

GENERAL FORMULA 5

Wherein Q is selected from aromatic ring systems including heterocycles such as phenyl, pyridyl, thienyl pyridazinyl, piperazinyl, pyrrolyl and quinolinyl nuclei, $R_1$ is H, lower alkyl, halogen, or lower alkoxy, and $R_2$ is H or an acyl group containing 1–4 carbons. However, when Q is phenyl then $R_1$ is not H.

Specific examples of compounds of the present invention which are shown by General Formula 5 are given below. The molar potency ratio (MPR) of each specific example and its melting point (m.p.) are also listed next to the specific example. The molar potency ratios of the compounds were determined in a manner which is generally known in the art, and is briefly described in the introductory portion of the present application for patent. Thus, examples of compounds of General Formula 5 are:

6-[2-(2-thienyl) ethyl amino]-9 -($\beta$-D-ribofuranosyl)-9H - purine; m.p. 153°–4°; MPR 4.01.

6-[2-(3-thienyl) ethyl amino]-9 -($\beta$-D-ribofuranosyl)-9H - purine; m.p. 152°–3°; MPR 2.48.

6-[2-(2-pyridyl) ethyl amino]-9 -($\beta$-D-ribofuranosyl)-9H - purine; m.p 124°–6°; MPR 0.83.

6-[2-(3-pyridyl) ethyl amino]-9 -($\beta$-D-ribofuranosyl)-9H - purine; m.p 165°–6°; MPR 3.16.

6-[2-(3-chlorophenyl) ethyl amino]-9 -($\beta$-D-ribofuranosyl)-9H - purine; m.p 128°–130°; MPR 1.34.

6-[2-(2-methoxyphenyl) ethyl amino]-9 -($\beta$-D-ribofuranosyl)-9H - purine; m.p 145°–6°; MPR 1.20.

6-[2-(3-methoxyphenyl) ethyl amino]-9 -($\beta$-D-ribofuranosyl)-9H - purine; m.p 110°–11°; MPR 1.25.

6-[2-(4-fluorophenyl) ethyl amino]-9 -($\beta$-D-ribofuranosyl)-9H - purine; m.p 190°–1°; MPR 1.6.

A specific example of the compounds of the present invention shown by General Formula 1, wherein X is C and n is 2, is 6 - (cyclobutyl amino]- 9 - ($\beta$-D-ribofuranosyl) - (9H -purine; m.p. 121°–3°. In the assay conducted on anesthetized healthy dogs, as described in the introductory section of the present application, this compound was found to have an MPR of 1.57.

Another specific example of the compounds of the present invention, shown by General Formula 1, is the hydrazino derivative 6 - (2-methyl-2-phenyl hydrazino)-9 -($\beta$-D-ribofuranosyl)-9H - purine (X is N, $R_2$ is phenyl, $R_3$ and $R_4$ are H in General Formula 1) m.p. 127°–9°; MPR 1.75.

Still another subgroup of the N-6 substituted adenosine derivatives of the present invention is shown by General Formula 6, wherein $R_1$ is methyl ethyl, propyl or hydroxymethyl, $R_2$ is methyl, ethyl, phenyl, lower alkyl substituted phenyl, lower alkoxy substituted phenyl, or monohalogen substituted phenyl, or other substituted or unsubstituted aromatic heterocycle, the chiral center in the two carbon chain may have either R or S configuration, and wherein $R_3$ is H, or acyl containing 1–4 carbons. However, when $R_1$ is methyl then $R_2$ is not phenyl.

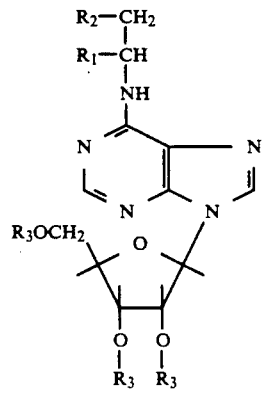

GENERAL FORMULA 6

Specific examples of compounds of General Formula 6 are:

(−)-6-(S-2-butyl amino)-9-($\beta$-D-ribofuranosyl)-9H-purine; m.p. 95°–8°; MPR 2.6, and its R enantiomer, m.p. 104°–105°; MPR 0.88.

6-(3-pentyl amino)-9-($\beta$-D-ribofuranosyl)-9H-purine; m.p. 90°–100°; MPR 4.0.

6-(4-heptyl amino)-9-($\beta$-D-ribofuranosyl)-9H-purine; m.p. 112°–113°; MPR 0.81.

(−)-6-(R-1-phenyl-2-butyl amino)-9-($\beta$-D-ribofuranosyl)-9H-purine; m.p. 135°–6°; MPR 7.5.

(+)-6-S-1-hydroxy-3-phenyl-2 propyl amino)-9-($\beta$-D-ribofuranosyl)-9H-purine; m.p. 96°–100°; MPR 1.6.

The high activity of (−)-6-(R-1-phenyl-2 butyl amino)-9-($\beta$-D-ribofuranosyl)-9H-purine is particularly important in view of the fact that the S enantiomer of this compound is substantially inactive.

Yet another subgroup of the compounds of the present invention is shown by General Formula 7, wherein $R_1$ is methyl or ethyl, $R_2$ is phenyl and $R_3$ is H, or acyl containing 1–4 carbons.

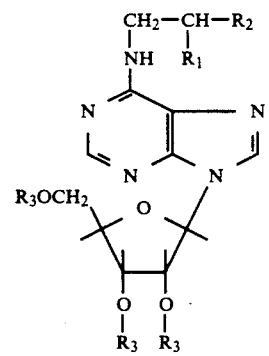

GENERAL FORMULA 7

Specific examples of the N-6 monosubstituted adenosine derivatives shown by General Formula 7 are:

(−)-6-(R-2-phenyl-1propyl amino)-9-($\beta$-D-ribofuranosyl)-9H-purine; m.p. 93°–95°; MPR 2.4; and the S enantiomer of this compound, m.p. 128°–9°; MPR 3.0.

6-(2-phenyl-1-butyl amino)-9-(β-D-ribofuranosyl)-9H-purine m.p. 96°–100°; MPR 3.5.

The N-6 monosubstituted adenosine derivatives of the present invention can be prepared, in accordance with the present invention by the following processes.

Purine nucleosides of General Formula 2, wherein Y represents a leaving group, are reacted with a primary amine or a hydrazino compound of the General Formula 3. The symbols $R_1$, $R_2$, $R_3$, $R_4$, $R_5$, X, m, n, p represent groups as defined above in connection with these two general formulae. Y is a suitable leaving group subject to nucleophilic displacement, and can be e.g. a chloro, bromo, iodo, mercapto, substituted benylmercapto, methylmercapto, benzylmercapto, mesyloxy, tosyloxy or trimethylsilyloxy group.

The hydroxyl groups of the ribofuranose moiety can remain unprotected for the nucleophilic displacement reaction. Alternatively, when desired, these hydroxyl groups can be protected by groups customarily used in sugar or nucleoside chemistry, such as acyl, benzyl or substituted benzyl groups. The 2′ and 3′ hydroxyl groups of the ribofuranose moiety may also be protected, when desired, by acid labile ketal or acetal groups, such as benzylidene or isopropylidene groups. As is known, during the nucleophilic displacement reaction acyl blocking groups of the sugar hydroxyls may be fully or partially cleaved. These groups are readily removed by alkali, for example by treatment with sodium methoxide in methanol. Benzyl blocking groups can be removed, by mild catalytic hydrogenation, and acetal and ketal blocking groups can be removed by acid.

6-chloro-9-(β-D-ribofuranosyl)-9H-purine, 6-chloro-9(tri-O-β-D-ribofuranosyl) - 9H purine, at 6-chloro-9-(tri-O-benzoyl-β-D-ribofuranosyl)-9H - purine are particularly suitable starting materials for the above-noted nucleophilic displacement reactions. Such starting compounds are described, for example, in Coll. Czech, Chem. Comm. 3-, page 1880 (1965), and in J. Org. Chem. 28, page 945 1963).

The nucleophilic displacement reactions between compounds of General Formulae 2 and 3 are advantageously conducted at elevated temperatures, in inert solvents, such as alcohols, ethers, pyridine or dimethylformamide. Ethanol, isopropanol, butanol, tetrahydrofurane, and dioxane are examples of suitable alcohol or ether type solvents.

Advantageously, an organic or inorganic acid acceptor, such as triethylamine, or calcium carbonate, or both are General Formula 3 may act as the acid acceptor.

The nucleophilic displacement reaction may also be conducted at room temperature, although in such a case the reaction times are prolonged relative to reactions at elevated temperature. In the event the reagent amine of General Formula 2 is low boiling the reaction may be conducted by heating the reactants in a sealed tube.

Conditions particularly suitable for conducting the nucleophilic displacement reaction when 6 chloro - 9 -(β-D-ribofuranosyl) - 9H - purine is the starting material, include heating the reactants for approximately twenty hours in refluxing ethanol, with the exclusion of atmospheric moisture, and in the presence of triethylamine and calcium carbonate. Alternatively, an even more preferred procedure is to reflux the reactants for approximately twenty hours in absolute ethanol in the presence of excess triethylamine. Preferably the course of the nucleophilic displacement reaction is monitored through thin layer chromatography, and the reaction is continued until completed.

In the event the Y leaving group gives rise to a volatile by-product, such as methylmercaptane or benzylmercaptane, then use of an acid acceptor is not necessary.

It should be understood, that instead of the free amines or hydrazino compounds shown in General Formula 3, their corresponding salts, such as the hydrobromide or hydrochloride, may also be used in the nucleophilic displacement reaction. Similarly, in the event the starting purine ribofuranoside of General Formula 2 contains an amino group, (for example when $R_1$ is an alkylamino or arylalkylamino group) then salts of these purine ribofuranosides are also suitable for use in the nucleophilic displacement reaction.

In addition to the above noted nucleophilic displacement reaction, certain 2-unsubstituted adenosine derivatives of the present invention, (compounds of General Formula 1 wherein $R_1$ is H and X is C) can also be obtained by hot alkali induced rearrangement of N-1 substituted adenosines, shown in General Formula 4.

In General Formula 4, $R_2$, $R_3$, $R_4$, $R_5$, m, p, and n define groups described above in connection with General Formula 1. $R_5$ also defines additional acyl blocking groups, as well as alkali stable benzyl, substituted benzyl, ketal and acetal blocking groups customarily used in carbohydrate and nucleoside chemistry.

The starting compounds of General Formula 4, are obtained, in a known manner, by alkylation of free adenosine, or of adenosine derivatives which are suitably protected in the ribofuranose moiety, with benzyl, ketal or acetal groups. The alkylating agents correspond in their alkyl moiety to the N-1 substituent of General Formula 4. Such alkylating agents must contain a suitable leaving group, such as a chloro, bromo, iodo, or an alkyl, aryl, alkylaryl or arylalkyl sulfonyloxy group.

As it should be readily appreciated by those skilled in the art, acyl blocking groups are usually removed from the ribofuranose moiety during the treatment with alkali which brings about the desired N-1 to N-6 rearrangement. Benzyl, ketal or acetal blocking groups, on the other hand, are readily removed, after the desired rearrangement by acidolysis or hydrogenation.

As still another, although less preferred process, compounds of the present invention may be obtained by N-9 glycosylation of the appropriately substituted purine derivatives. The glycosylation can be conducted under known conditions, such as heating of the appropriately substituted purines with tri-0-benzoyl - D-ribofuranosyl chloride or bromide in nitromethane in the presence of a mercury salt.

The compounds of the present invention are useful as cardiac vasodilators, in mammals, domestic animals and humans. Although various modes of administering the compounds may become apparent oral and topical administration and intravenous infusion are presently preferred. Activity of the compounds as coronary vasodilators is reflected by their molar potency ratio number. Several pharmacologically accepted salts of the compounds of the present invention can also be used as vasodilators.

SPECIFIC EXAMPLE

6-[2-(2-thienyl)ethyl]amino-9-($\beta$-D-ribofuranosyl)-9H-purine

A mixture of 6 - chloro - 9 ($\beta$-D-ribofuranosyl) - 9H - purine (1.5 g, 5.2 mmoles), 2-(2- aminoethyl)thiophene (0.7 g, 5.5 mmoles) (the hydrochloride of the amine can also be used), triethylamine (2.2 ml, 15.6 mmoles) and 50 ml of absolute ethanol was refluxed for 20 hours. The solvents were removed in vacuo. Ether was added to the residue, which precipitated the amine hydrochloride. The amine hydrochloride was removed by filtration and the solvents were removed in vacuo to give a foam. The foam was recrystallized from methanol to give 1.5 g (76% as colorless needles, mp 153°-154°; u.v:λmax ($\epsilon$), 270 nm (18,500) at pH 7; nmr (DMSO-d$_6$): 3.15 (t, 2H, CH$_2$-2), 3.52-5.50 (m, 10H, CH$_2$-1 and ribose), 5.88 (d, 1H, anomeric, J$_{1,2}$= 5.8 Hz), 6.92 [m, 2H, thienyl (H-3 and H-4)],7.29 (br t, 1H, NH), 8.22 (s, 1H, H-8), 8.32 (s, 1H, H-2).

Anal Calcd. for C$_{16}$H$_{19}$N$_5$O$_4$S.1/2H$_2$O (386.43): C, 49.73; H, 5.22; N, 18.12; S, 8.30; Found: C, 50.00; H, 5.20; N, 18 12; S, 8.17.

What is claimed is:

1. A method of administering a compound of the formula

GENERAL FORMULA I

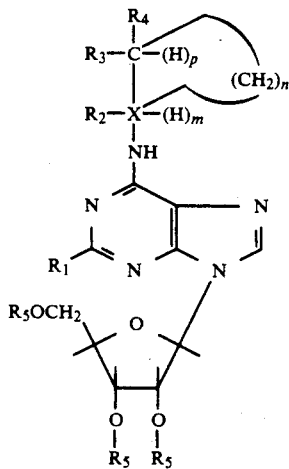

wherein R$_1$ is H, a C$_1$ to C$_4$ lower alkyl group or an alkoxy group having 1–4 carbon atoms;

R$_2$ is H, C$_1$–C$_4$ lower alkyl group, hydroxymethyl group, phenyl group, C$_1$–C$_4$ lower alkyl substituted phenyl group, C$_1$–C$_4$ lower alkoxy substituted phenyl group;

R$_3$ is H, C$_1$–C$_4$ lower alkyl group, phenyl group, C$_1$–C$_4$ lower alkyl substituted phenyl group, mono-halogen substituted phenyl group, C$_1$–C$_4$ mono-lower alkoxy substituted phenyl group, 2 or 3-thienyl group, C$_1$–C$_4$ lower alkyl substituted 2 or 3-thienyl group, C$_1$–C$_4$ lower alkoxy substituted 2 or 3-thienyl group, mono-halogen substituted 2 or 3-thienyl group, 2 or 3-pyridyl group, C$_1$–C$_4$ lower alkyl substituted 2 or 3-pyridyl group, C$_1$–C$_4$ lower alkoxy substituted 2 or 3-pyridyl, pyridazinyl, piperazinyl, pyrollyl or quinolinyl group, or mono-halogen substituted 2 or 3-pyridyl group;

R$_4$ is H, or a C$_1$–C$_4$ lower alkyl group;

R$_5$ is H, or an acyl group having 1–4 carbons;

X is C or N;

n is either 0 (zero) or 2;

m is either 0 (zero) or 1;

p is either 0 (zero) or 1;

with the provisos that when X is N then n is 0, m is 0 and p is 1, when X is C and n is 0 then m is 1 and p is 1, when X is C and n is 2, then m is 0 and p is 0 and when X is C, n is 0, R$_2$ is methyl, R$_1$ and R$_4$ are H, then R$_3$ is not phenyl;

to a mammal in need thereof, including humans and domestic animals, in an effective dosage of said compound to obtain a cardiovascular vasodilatory effect.

2. The method of claim 1 wherein R$_1$ is H, R$_2$ is H, R$_4$ is H, X is C, n is 0 (zero), and R$_3$ is selected from a group consisting of 2-thienyl, 3-thienyl, 2-pyridyl, 3-pyridyl, mono-halogen substituted phenyl and C$_1$–C$_4$ mono-alkoxy substituted phenyl groups.

3. The method of claim 2 wherein R$_5$ is H.

4. The method of claim 3 wherein R$_3$ is 2-thienyl.

5. The method of claim 3 wherein R$_3$ is 3-thienyl.

6. The method of claim 3 wherein R$_3$ is 3-pyridyl.

7. The method of claim 3 wherein R$_3$ is 2-pyridyl.

8. The method of claim 3 wherein R$_3$ is 3-chlorophenyl.

9. The method of claim 3 wherein R$_3$ is 2-methoxyphenyl.

10. The method of claim 3 wherein R$_3$ is 4-fluorophenyl.

11. The method of claim 1 wherein R$_1$ is H, R$_2$ is H, R$_3$ is H, R$_4$ is H, X is C and n is 2.

12. The method of claim 11 wherein R$_5$ is H.

13. The method of claim 1 wherein R$_1$ is H, R$_2$ is phenyl, R$_3$ is H, R$_4$ is H and X is N.

14. The method of claim 13 wherein R$_5$ is H.

15. The method of claim 1 wherein R$_1$ is H, R$_2$ is methyl, ethyl, propyl or hydroxymethyl, R$_3$ is methyl, ethyl, phenyl, C$_1$–C$_4$ lower alkoxy substituted phenyl or mono-halogen substituted phenyl, R$_4$ is H, X is C and n is 0 (zero).

16. The method of claim 15 wherein R$_2$ is ethyl, R$_3$ is methyl and R$_5$ is H.

17. The method of claim 15 wherein R$_2$ is propyl, R$_3$ is ethyl and R$_5$ is H.

18. The method of claim 1 wherein R$_1$ is H, R$_2$ is H, R$_3$ is methyl or ethyl, R$_4$ is phenyl, C$_1$–C$_4$ lower alkyl substituted phenyl, C$_1$–C$_4$ lower alkoxy substituted phenyl, mono-halogen substituted phenyl, X is C and n is 0 (zero).

19. The method of claim 18 wherein R$_4$ is phenyl.

20. The method of claim 19 wherein R$_3$ is methyl and R$_5$ is H.

21. The method of claim 19 wherein R$_3$ is ethyl and R$_5$ is H.

22. A method according to claim 1 wherein said compound is (−) -6-(S-2-butylamino)-9-($\beta$-D-ribofuranosyl)-9H-purine.

23. A method according to claim 1 wherein said compound is (−)-6-(R-1-phenyl-2-butylamino)-9-($\beta$-D-ribofuranosyl)-9H-purine.

24. A method according to claim 1 wherein said compound is (+)-6-(S-1-hydroxy-3-phenyl-2-propylamino)-9-($\beta$-D-ribofuranosyl)-9H-purine.

25. A method according to claim 1 wherein said compound is (−)-6-(R-2-phenyl-1-propylamino)-9-($\beta$-D-ribofuranosyl)-9H-purine.

26. A method according to claim 1 wherein said compound is (+)-6-(S-2-phenyl-1-propylamino)-9-($\beta$-D-ribofuranosyl)-9H-purine.

* * * * *